United States Patent [19]

Thottathil et al.

[11] Patent Number: 4,501,901

[45] Date of Patent: Feb. 26, 1985

[54] METHOD FOR MAKING SUBSTITUTED PROLINES

[75] Inventors: John K. Thottathil, Trenton; Jerome L. Moniot, Chester; David Floyd, Pennington; Steven Brandt, Plainsboro, all of N.J.

[73] Assignee: E. R. Squibb & Sons, Inc., Princeton, N.J.

[21] Appl. No.: 533,705

[22] Filed: Sep. 19, 1983

[51] Int. Cl.³ .......................................... C07D 207/12
[52] U.S. Cl. ..................................... 548/532; 548/533
[58] Field of Search ............................... 548/532, 533

[56] References Cited

U.S. PATENT DOCUMENTS 4,316,905  2/1982  Krapcho .............................. 424/274
4,316,906  2/1982  Ondetti et al. ...................... 424/274

OTHER PUBLICATIONS

Johnson, et al., J.A.C.S., 95, (1973), pp. 7783–7787.
Still, et al., J.A.C.S., 104, (1982), pp. 1774–1776.
Organic Reactions, vol. 22, (1975), pp. 275, 276, 285, 301, 302, 326, 381, 383.
Fieser and Fieser; Reagents for Organic Synthesis, (1969), vol. 2, pp. 151, 152, John Wiley & Sons, N.Y.
Fieser and Fieser; Reagents for Organic Synthesis, vol. 3, (1972), pp. 106, 107, John Wiley & Sons, N.Y.
Fieser and Fieser, Reagents for Organic Synthesis, vol. 4, (1974), pp. 180, 181, 182, 183, John Wiley & Sons, N.Y.
Fieser and Fieser, Reagents for Org. Syn., vol. 5, (1975), pp. 234, 235, 240, John Wiley & Sons, N.Y.
Fieser and Fieser, Reagents for Org. Syn., vol. 6, (1977), pp. 209, 210, 211, 234, John Wiley & Sons, N.Y.

Primary Examiner—Joseph Paul Brust
Attorney, Agent, or Firm—Lawrence S. Levinson; Burton Rodney

[57] ABSTRACT

A method is provided for making substituted prolines of the structure

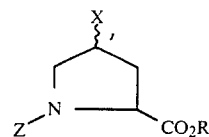

wherein X is lower alkyl or aryl, R is H, lower alkyl or an alkali metal and Z is an N-protecting group, which method includes the step of reacting a compound of the structure

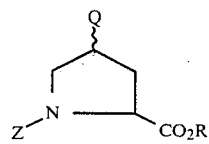

wherein Z and R are as defined above and Q is Br, tosyloxy or mesylate, with an organic copper lithium compound of the structure XYCuLi wherein X is as defined above and Y is lower alkyl, aryl or CN.

Where X is phenyl, the corresponding 4-cyclohexyl compound may be produced by conventional hydrogenation techniques.

The compounds produced are useful as intermediates in the preparation of phosphinic acid derivatives useful in the treatment of hypertension.

7 Claims, No Drawings

METHOD FOR MAKING SUBSTITUTED PROLINES

FIELD OF THE INVENTION

The present invention relates to a method for preparing substituted prolines having the structure

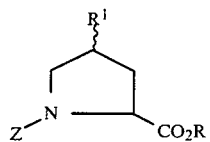

wherein R is H, lower alkyl or an alkali metal, $R^1$ is aryl, lower alkyl or cyclohexyl, Z is a chemically removable N-protecting group, and the wavy line ( ) indicates that $R^1$ is either trans or cis to the proline ring. The above substituted prolines are useful as intermediates in the preparation of phosphinic acid angiotensin-converting enzyme inhibitors such as described in U.S. Pat. Nos. 4,316,905 and 4,316,906.

BRIEF DESCRIPTION OF THE INVENTION

The method in accordance with the present invention for making intermediate compounds of the structure

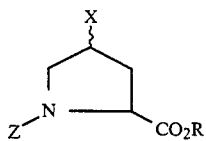

wherein X is aryl or lower alkyl, R is H, lower alkyl or an alkali metal, and Z is a chemically removable N-protecting group, includes the steps of providing a compound of the structure

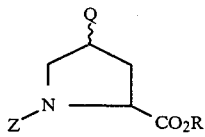

wherein Z and R are as defined above and Q is Br, tosyloxy or mesyloxy, and reacting the formula III compound with an organic copper lithium compound of the structure

 XYCuLi      IV wherein X and Y may be the same or different and X is lower alkyl or aryl and Y is lower alkyl, aryl or CN, to form the formula II compound.

The method of the present invention also encompasses the preparation of the 4-cyclohexyl intermediate of the structure

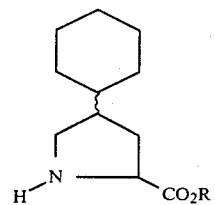

wherein Z and R are as defined above which method includes the step of forming the 4-phenyl intermediate of the structure

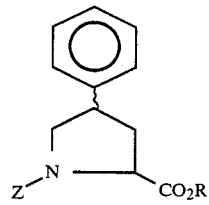

wherein Z and R are as defined above, by reacting a compound of structure III with diphenylcopper lithium $((C_6H_5)_2CuLi)$ or $C_6H_5(CN)CuLi$, removing the Z nitrogen protecting group, for example, by reaction with trifluoroacetic acid, to form

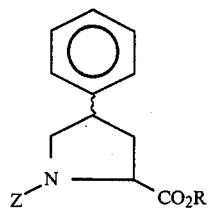

and then hydrogenating the 4-phenyl derivative VII to form the corresponding 4-cyclohexyl derivative V.

The term "lower alkyl" as used in defining the symbols X, R and $R^1$ includes straight or branched chain hydrocarbon radicals having up to 7 carbons, for example, methyl, ethyl, propyl, isopropyl, butyl, isobutyl, t-butyl, pentyl, isopentyl, etc. The preferred lower alkyl groups are up to 4 carbons with methyl and ethyl being most preferred.

The term "aryl" as used in defining the symbols X and $R^1$ includes phenyl, 1-naphthyl, 2-naphthyl, and biphenyl. The terms substituted aryl, substituted phenyl, and substituted phenyl-lower alkylene includes such groups having one or two, preferably one, substituent on the ring. Suitable substituents include lower alkyl groups of 1 to 4 carbons, especially methyl, lower alkoxy groups of 1 to 4 carbons, especially methoxy, lower alkylthio groups of 1 to 4 carbons, especially methylthio, halogens, especially chloro or fluoro, trifluoromethyl, acetyloxy, and hydroxy. The hydroxy substituted aryl, phenyl and phenyl-lower alkylenes are obtained by hydrolysis of the corresponding acetyloxy substituted phenyl compounds as the last step of the synthetic procedure.

The term "chemically removable protecting group" employed in defining Z refers to groups such as p-methoxybenzyl, p-methoxybenzyloxycarbonyl, t-butoxycarbonyl, etc. These groups can be removed without affecting the remainder of the molecule such as by treating with trifluoroacetic acid and anisole.

DETAILED DESCRIPTION OF THE INVENTION

In carrying out the method of the invention to prepare compounds of formula II, that is, where X is aryl or lower alkyl, the starting material of formula III where R is H will be employed in a molar ratio to the organic copper lithium compound IV of within the range of from about 1:1.5 to about 1:10 and from about 1:1.7 to about 1:1.2, and optimally about 1:2. Where in the starting material of formula III, R is lower alkyl or alkali metal, then, the formula III compound will be employed in a molar ratio to the organic copper lithium compound IV of within the range of from about 0.5:1 to about 1:10, preferably from about 0.7:1 to about 1:1.5, and optimally about 1:1.

The above reaction between compounds of formulae III and IV, will be carried out at a temperature of within the range of from about −25° C. to about 25° C., and preferably from about −20° C. to about 20° C., for a period of from about 1 to about 15 hours and preferably from about 2 to about 7 hours, in the presence of an inert solvent such as tetrahydrofuran, ethyl ether and the like.

Furthermore, in accordance with the method of the invention, where it is desired to form the 4-cyclohexyl compound of formula V, the 4-phenyl intermediate of formula VI will be reacted with, for example, trifluoroacetic acid, to remove the nitrogen protecting group to form

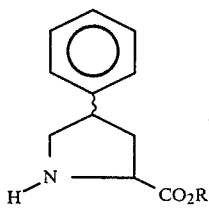

VII which will then be hydrogenated, employing conventional techniques, for example by reaction with hydrogen in the presence of a platinum or palladium on charcoal catalyst to form the 4-cyclohexyl derivative V.

The esters of formula II wherein R is lower alkyl can be obtained from the carboxylic acid compounds, i.e., wherein R is hydrogen, by conventional esterification procedures, e.g., by esterification with a diazomethane, a 1-alkyl-3-p-tolyltriazene, such as 1-n-butyl-3-p-tolyltriazene, etc. or by reaction with an alcohol in the presence of sulfuric acid.

If the proline of formula III is reacted in the ester form the resulting ester product of formula II, i.e., R is alkyl, can be converted to the free acid, i.e., R is hydrogen, by conventional means. For examle, if R is t-butyl, this ester protecting group can be removed by treatment with trifluoroacetic acid and anisole. If R is $CH_3$, this ester group can be removed by hydrolyzing in the presence of sodium hydroxide.

The compounds of formula I, II or V where R is an alkali metal may be prepared by simply reacting the corresponding carboxylic acid with the appropriate alkali metal (Li, Na or K) salt, such as lithium bicarbonate, sodium bicarbonate or potassium bicarbonate.

As shown in formula I or II, the substituent X or $R^1$ may be in the trans or cis-configuration, preferably the trans-configuration, with respect to the asymmetric center in the proline ring which is in the L-configuration. The intermediates of formulae I, II and V can accordingly exist in stereoisomeric forms or as racemic mixtures thereof. All of these are within the scope of the invention. The synthesis described below can utilize the racemate or one of the enantiomers as starting materials. When the racemic starting material is used in the synthesis procedure, the stereoisomers obtained in the final product can be separated by conventional chromatographic or fractional crystallization methods.

The starting materials of formula II may be prepared according to the procedure of Portoghese et al., Tetrahedron, Vol. 27, p. 961–967 or as described in U.S. Pat. Nos. 4,316,905 and 4,316,906.

As indicated in U.S. Pat. Nos. 4,316,905 and 4,316,906, the starting material may be obtained as a mixture of cis- and trans-isomers with respect to the $CO_2R$ group. The mixture can be separated into the individual cis- and trans-isomers at this point of the synthetic procedure and the isomers can be purified by crystallization, by conversion to a salt form, such as the l-adamantanamine salt, or by chromatographic means.

The starting copper-lithium compound IV may be prepared by reacting cuprous bromide or cuprous bromide dimethyl sulfide complex or cuprous cyanide with an aryl or alkyl lithium compound in an inert solvent suh as tetrahydrofuran or ethyl ether.

The following Examples represent preferred embodiments of the present invention. Unless otherwise indicated, all temperatures are expressed in degrees Centigrade.

EXAMPLE 1

(trans)-4-Phenyl-L-proline

A. N-t-Butoxycarbonyl-trans-4-hydroxy-L-proline

4-Hydroxyproline (31.2 g. 0.238 mole) was dissolved in sodium hydroxide (9.5 g) in water (75 ml) and t-butanol (50 ml) and to that was added with stirring and ice-cooling, a solution of di-tert-butyl-dicarbonate (57.1 g, 0.262 mole) in t-butanol (50 ml) and the stirring was continued overnight at ambient temperature. Water (125 ml) was added to the reaction mixture and was extracted with hexanes (2×100 ml). The aqueous layer was acidified with $KHSO_4$ (~35 g in 150 ml $H_2O$) in an ice bath to a pH~2 or 3. It was extracted with ethylacetate (4×100 ml) and the combined organic phase was washed with brine and dried over anhydrous sodium sulfate. Removal of the solvent on a rotavap gave a glassy solid in 100% yield, m.p. 124° C. This material was used for the next step without any further purification.

Anal. Calc'd for $C_{10}H_{17}O_5N$: C, 51.95; H, 7.36; N, 6.06. Found: C, 51.67; H, 7.37; N, 5.92.

B. N-t-Butoxycarbonyl-2-benzoyloxy-trans-4-hydroxy-L-proline

To an ice-cold solution of N-t-butoxycarbonyl-4-hydroxy proline (prepared as in Part A) (55.82 g, 0.24165 mole) in acetone (200 ml) was added benzyl bromide (43.11 ml, 0.3625 mole) followed by triethylamine (50.43 ml, 0.3625 mole). The reaction mixture was stirred at room temperature for 1 hour and heated to reflux, with stirring, for 12 hours. Acetone was removed on a rotavap and the residue obtained was dissolved in water (~250 ml) and extracted with ether (3×100 ml). The combined organic phase was washed with 5% sodium bicarbonate (2×50 ml), water (1×50 ml) and brine (50 ml), respectively. It was dried (Na₂SO₄) and the solvents removed on a rotavap to give the benzyl ester as a yellow oil. 57.6 g. TLC, single spot (Silica gel, CHCl₃—MeOH—HOAc; 95:0.2:0.2). $R_f$=0.5. This material was used for the next step without any further purification.

C. N-t-Butoxycarbonyl-2-benzoyloxy-trans-4-tosyloxy-L-proline

To an ice-cold solution of the intermediate from Part B (57.16 g, 0.178 mole) in pyridine (225 ml) was added tosyl chloride (33.95 g, 0.178 mole) in pyridine (50 ml). The reaction mixture was heated in a pre-heated oil bath at 40° C. and stirred for 5 hours. An additional amount of tosyl chloride (33.9 g, 0.178 mole) in pyridine (50 ml) was added to the cooled reaction solution and after the addition, it was heated at 40° C. overnight. The reaction mixture was poured into ice (~1000 g). Water was decanted off from the gummy solid, separated and the solid was dissolved in ethyl acetate (500 ml), washed with water (2×100 ml), 1N ice-cold HCl acid (2×100 ml), saturated NaHCO₃ (2×100 ml) and brine (2×100 ml), respectively. The organic phase was dried over anhydrous sodium sulfate and the solvent was removed on a rotavap to give 76.46 g of crude solid. (This material was used for the next step without any further purification). An analytical sample was prepared by crystallization from ether:hexane to give the title C compound in the form of a hard rocky white solid, m.p. 75°–76° C.

Anal Calc'd for C₂₄H₂₉O₇NS: C, 60.63; H, 6.11; N, 2.95; S, 6.74. Found: C, 60.69; H, 6.16; N, 2.93; S, 6.49.

D. N-t-Butoxycarbonyl-trans-4-tosyloxy-L-proline

To a solution of the intermediate in Part C (44.3 g, 0.09326 mole) in ethyl acetate (150 ml) was added palladium on charcoal (10%, 4.5 g) and the mixture was hydrogenated on a Parr shaker at ambient temperature overnight at 40 psi. Filtration followed by removal of the solvent on a rotavap gave white crystalline material, m.p. 147°–148° C. (Yield from crude title D was 83.02% based on title C intermediate and yield from pure title D compound was quantitative.).

Anal Calc'd for C₁₇H₂₃O₇S: C, 52.99; H, 5.97; N, 3.64; S, 8.31. Found: C, 52.87; H, 6.07; N, 3.57; S, 8.26.

$[\alpha]_D = -53.3°$ [10 mg/ml CHCl₃].

E. (trans)-4-Phenyl-L-proline

To a suspension of CuBr:

(27.02 g, 0.13143 mole) in dry ether (600 ml) was added phenyllithium (111.58 ml, 2.355 molar solution, 0.2629 mole) dropwise keeping the inside temperature between −20° to −15° C. At the end of the addition a bright clear yellow solution was obtained which was stirred at that temperature for another 15 minutes. A solution of Title D tosylate acid (23.0 g, 0.597 mole) in THF (dry, 300 ml) was added to the diphenyl copper lithium solution at −15° C. and the reaction mixture was stirred at that temperature for 2 hours and 1 hour at 0° C. and allowed to come to ambient temperature (1 hour) followed by 1 hour at ambient temperature. It was cooled in an ice bath and saturated ammonium chloride solution (200 ml) was added to it with vigorous stirring and left overnight at room temperature. The pH of the solution was raised from 11 to 12 by adding 10% NaOH solution, and the solution was then extracted with ether. The blue aqueous phase was acidified with 10% KHSO₄ to a pH of ~1 to 2 with cooling and stirring and the solution was then extracted with ethyl acetate (4×100 ml). The combined organic phase was washed with water (2×50 ml) and brine (2×50 ml) and dried over anhydrous magnesium sulfate. Removal of the solvent on a rotavap gave 15.5 g (89%) of crude phenyl substituted material, namely, N-t-butoxycarbonyl-4-phenylproline, as heavy white crystals. The above crude material was dissolved in chloroform (50 ml) and trifluoroacetic acid (50 ml) was added to it, and the mixture stirred at room temperature for 1 hour and the solvent evaporated on a rotavap. Toluene (100 ml) was added to the residue and evaporated again on a rotavap. The residue was dissolved in 500 ml water (pH ~1) and the pH of the solution was brought to 6.3 by adding 10% NaOH solution. The precipitate was dissolved in 2 liters hot water and ~2 g of charcoal was added to it and boiled for 5 minutes, filtered and concentrated to a volume of ~500 ml. It was kept in the refrigerator overnight to complete the crystallization. It was filtered, washed with water (50 ml), acetonitrile (100 ml), and ether (100 ml) and air dried to give 6 g of title compound, m.p. >300° C.

$[\alpha]_D = +22.3°$ (10 mg/1N HCl acid).

Anal. Calcd for C₁₁H₁₃NO₂: C, 69.11; H, 6.81; N, 7.33. Found: C, 69.05; H, 6.84; N, 7.12.

TLC, Silica gel, CH₂Cl₂—MeOH—HOAc (6:2:2); $R_f$=0.3.

EXAMPLE 2

(trans)-4-Phenyl-L-proline

A. N-t-butoxycarbonyl-trans-4-phenyl-L-proline

To a suspension of CuBr:

(5.47 g, 0.266 mole) in dry ether (130 ml) was added phenyllithium (23.77 ml, 0.05325 moles) dropwise, keeping the inside reaction temperature between −15° to −20° C. At the end of the addition, a bright yellow clear solution was obtained which was stirred at that temperature for 15 minutes. This diphenyl copper lithium solution was added to a solution of Example 1 title D tosylate acid (5.0 g, 0.01299 mole) in dry THF (65 ml) using a double ended needle and keeping the reaction temperature between 0° to +2° C. After the addition, the reaction temperature was maintained between +5° to +8° C. At the end of 1 hour and 10 minutes, all the starting material was consumed (TLC, CH₂Cl₂—MeOH; 4:1) and the reaction mixture was cooled to −10° C. and saturated ammonium chloride (50 ml) was added to it with vigorous stirring. The resulting mixture was left overnight at room temperature. The pH of the aqueous phase was brought to 11 to 12 by adding 10% NaOH solution and extracted with ether (3×100 ml). The deep blue aqueous solution was acidified with 10% KHSO₄ to pH 1 to 2 and extracted with ethyl acetate (3×200 ml) and the combined organic phase was washed with water (2×50 ml) and brine (2×50 ml) and dried over anhydrous magnesium sulfate. On removal of the solvent on a rotavap, crude Title A compound was obtained as heavy white crystals (3.77 g). It was crystallized from diisopropylether to give 2.77 g of title A compound (71%) as a single pure isomer, m.p. 155°–156° C.

$[\alpha]_D = -66.6°$ (10 mg/ml CHCl$_3$).

TLC: Silica gel, CH$_2$Cl—MeOH (4:1); Rf=0.45.

B. (trans)-4-Phenyl-L-proline

A solution of pure t-butyloxycarbonyl-acid from part A (0.1 g, 0.000344 mole) in CH$_2$Cl$_2$ (5 ml) was cooled in an ice bath and trifluoroacetic acid (5 ml) was added to it. The reaction mixture was stirred at room temperature for 1 hour and the solvent removed on a rotavap to give an oil. Toluene (25 ml) was added to the oil and the mixture was rotavaporated and high vacuum dried and the process repeated 2 more times to give title compound as a grey crystalline material, 0.066 g (100%).

$[\alpha]_D = +22.0°$.

TLC: silica gel, CH$_2$Cl$_2$:MeOH:HOAc (6:2:2), Rf=0.3 (single spot) and HPLC single peak. 400 MHz NMR spectrum was identical to that obtained by the method of Example 1.

EXAMPLE 3

(trans)-4-Phenyl-S-proline

Phenyllithium (23.77 ml, 0.05325 mole) was added to a suspension of cuprous bromide dimethyl sulfide complex (5.47 g, 0.02662 mole) in ether (130 ml) at −15° C. After the addition, it was stirred for 15 minutes. The proline derivative prepared in Example 1, part D (5.0 g, 0.12989 mole) in dry tetrahydrofuran (60 ml) was added to the above mixture and the reaction temperature kept at +5° to +8° C. After 1 hour, all the starting material was consumed and the mixture was cooled in ice and quenched by adding saturated ammonium chloride solution (20 ml) and left at room temperature overnight.

pH of the solution was brought to 12 by adding 10% NaOH solution and the solution was then extracted with ether. The blue aqueous solution was acidified with 10% KHSO$_4$ to pH 1 to 2 and extraction workup produced the title compound in 71% yield as pure white crystals.

EXAMPLE 4

(trans)-4-Cyclohexyl-S-proline

To a solution of (trans)-4-phenyl-L-proline (0.51 g, 0.0027 mole) produced as described in Example 1 in 25 ml ethanol and 4.3 ml 2.24% HCl acid in ethanol was added platinum dioxide (0.1 g) and the mixture was hydrogenated on a Parr shaker at ambient temperature overnight at 40 psi. Filtration followed by removal of the solvent on a rotavap produced the title product, 0.58 g, 93%, as a white crystalline solid as its hydrochloride salt.

EXAMPLE 5

(trans)-4-Phenyl-L-proline

In a manner similar to the procedure described in Example 1, except substituting N-t-butoxycarbonyl-trans-4-bromo-L-proline for N-t-butoxycarbonyl-trans-4-toxyloxy-L-proline, the title compound is obtained.

EXAMPLE 6

(trans)-4-Ethyl-L-proline

In a manner similar to the procedure described in Example 1, except substituting diethyl copper lithium for diphenyl copperlithium, the title compound is obtained.

EXAMPLE 7

(cis)-4-Phenyl-L-proline

In a manner similar to the procedure described in Example 1, except substituting N-benzyloxycarbonyl-cis-4-tosyloxy-L-proline methyl ester for title D tosylate acid and after the reaction removing the methyl ester by sodium hydroxide hydrolysis and N-benzyloxycarbonyl group by hydrogenation over palladium catalyst, the title compound is obtained.

EXAMPLE 8

4-trans-Phenyl-(S)-proline

To a magnetically stirred suspension of 19.25 g (215 mmol) CuCN in 215 ml dry THF under argon at 0° C. was added 82.7 ml (215 mmol) of 2.6M phenyl lithium. The mixture was then allowed to stir at ambient temperature for 1 hour. The trans-tosylate (15.59 g, 35.9 mmol) was then added as a degassed solid and the reaction allowed to stir for 3 hours. The reaction mixture was then poured into 360 ml of magnetically stirred saturated aqueous NH$_4$Cl. After filtration, the resulting two layers were separated and the aqueous layer extracted with CH$_2$Cl$_2$. The combined organic layers were dried over anhydrous MgSO$_4$, filtered and rotary evaporated. To the residue was added 180 ml THF followed by 720 ml of 0.5N NaOH. After stirring for 3 hours, the mixture was acidified to pH 2 with concentrated HCl and extracted with CH$_2$Cl$_2$. The combined organic layers were dried over anhydrous MgSO$_4$, filtered, and rotary evaporated leaving a yellow gum. The gum was then hydrogenated for 3 hours under H$_2$ using 400 ml CH$_3$OH, 60 ml 10% aqueous HCl and 1.5 g 10% Pd/C. The mixture was then filtered and rotary evaporated. The residue was dissolved in 200 ml H$_2$O with warming and a solution of 1.44 g NaOH in 100 ml H$_2$O was added. An additional amount of 1N NaOH was added to bring the solution to pH 6. This solution was then filtered through a millipore filter and the solution boiled down to a volume of 300 ml. The solution was then cooled gradually and the resulting crystals collected to yield 3.16 g (46%) of title compound in the form of light brown crystals.

What is claimed is:

1. A method for making substituted prolines of the structure

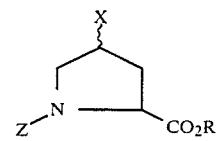

wherein X is phenyl, 1-naphthyl, 2-naphthyl, biphenyl or lower alkyl having up to 7 carbons, R is H, lower alkyl having up to 7 carbons or an alkali metal, Z is a chemically removable N-protecting group and the wavy line ( ⌇ ) indicates that X is either trans or cis to the proline ring, which comprises reacting a compound of the structure

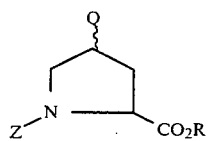

wherein Z and R are as defined above and Q is Br, tosyloxy or mesyloxy, and the wavy line ( ) indicates that Q is either trans or cis to the proline ring, with an organic copper lithium compound of the structure XYCuLi wherein X and Y may be the same or different and X is as defined above and Y is phenyl, 1-naphthyl, 2-naphthyl, biphenyl, lower alkyl having up to 7 carbons or CN, to form a compound of the structure

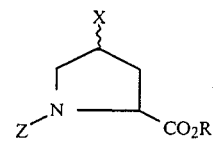

wherein X is trans to the proline ring where Q is trans to the proline in the starting material or X is cis to the proline ring where Q is cis to the proline ring in the starting material.

2. The method as defined in claim 1 wherein X is phenyl.

3. The method as defined in claim 1 wherein X is lower alkyl.

4. The method as defined in claim 1 wherein Z, the N-protecting group, is

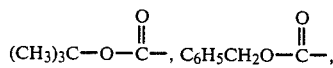

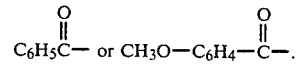

5. The method as defined in claim 1 wherein X is cis to the proline ring.

6. The method as defined in claim 1 wherein R is H or alkyl.

7. The method as defined in claim 1 wherein X is trans to the proline ring.

* * * * *